United States Patent

Pomatto et al.

[11] Patent Number: 5,308,312
[45] Date of Patent: May 3, 1994

[54] CRANIAL REMODELING ORTHOSIS

[76] Inventors: R. Craig Pomatto; Jeanne K. Pomatto, both of 24200 N. Alma School Rd., #35, Scottsdale, Ariz. 85255

[21] Appl. No.: 26,774

[22] Filed: Mar. 5, 1993

[51] Int. Cl.⁵ .............................................. A61F 5/00
[52] U.S. Cl. ............................................. 602/17; 2/414
[58] Field of Search .......................... 2/411, 412, 414; 602/17; 128/845, 846, 857

[56] References Cited

U.S. PATENT DOCUMENTS

| | | | |
|---|---|---|---|
| 1,569,181 | 1/1926 | Hartman | 2/414 |
| 1,576,987 | 3/1926 | Mullins | 2/414 |
| 2,758,304 | 8/1956 | McGowan | 2/411 |
| 3,364,499 | 1/1968 | Kwoka | 2/414 |
| 3,577,562 | 5/1971 | Holt | 2/414 |
| 4,352,352 | 10/1982 | Janovsky et al. | 602/17 |
| 4,645,198 | 2/1987 | Levenston | 602/17 X |
| 4,776,324 | 10/1988 | Clarren | 602/17 |
| 5,094,229 | 3/1992 | Pomatto et al. | |
| 5,119,516 | 6/1992 | Broersma | 2/412 X |
| 5,177,815 | 1/1993 | Andujar | 2/411 |

FOREIGN PATENT DOCUMENTS

| | | | |
|---|---|---|---|
| 2509585 | 1/1983 | France | 2/411 |
| 0659134 | 4/1979 | U.S.S.R. | 2/412 |

Primary Examiner—Richard J. Apley
Assistant Examiner—Linda C. M. Dvorak
Attorney, Agent, or Firm—Cahill, Sutton & Thomas

[57] ABSTRACT

A cranial remodeling orthosis is shaped to extend across the top of the head with depending regions closely confining the temporal bone regions and the mastoid process regions of the cranium. The orthosis is self-suspending and preferably includes an elastic band for imparting ear-to-ear rigidity to the device.

4 Claims, 1 Drawing Sheet

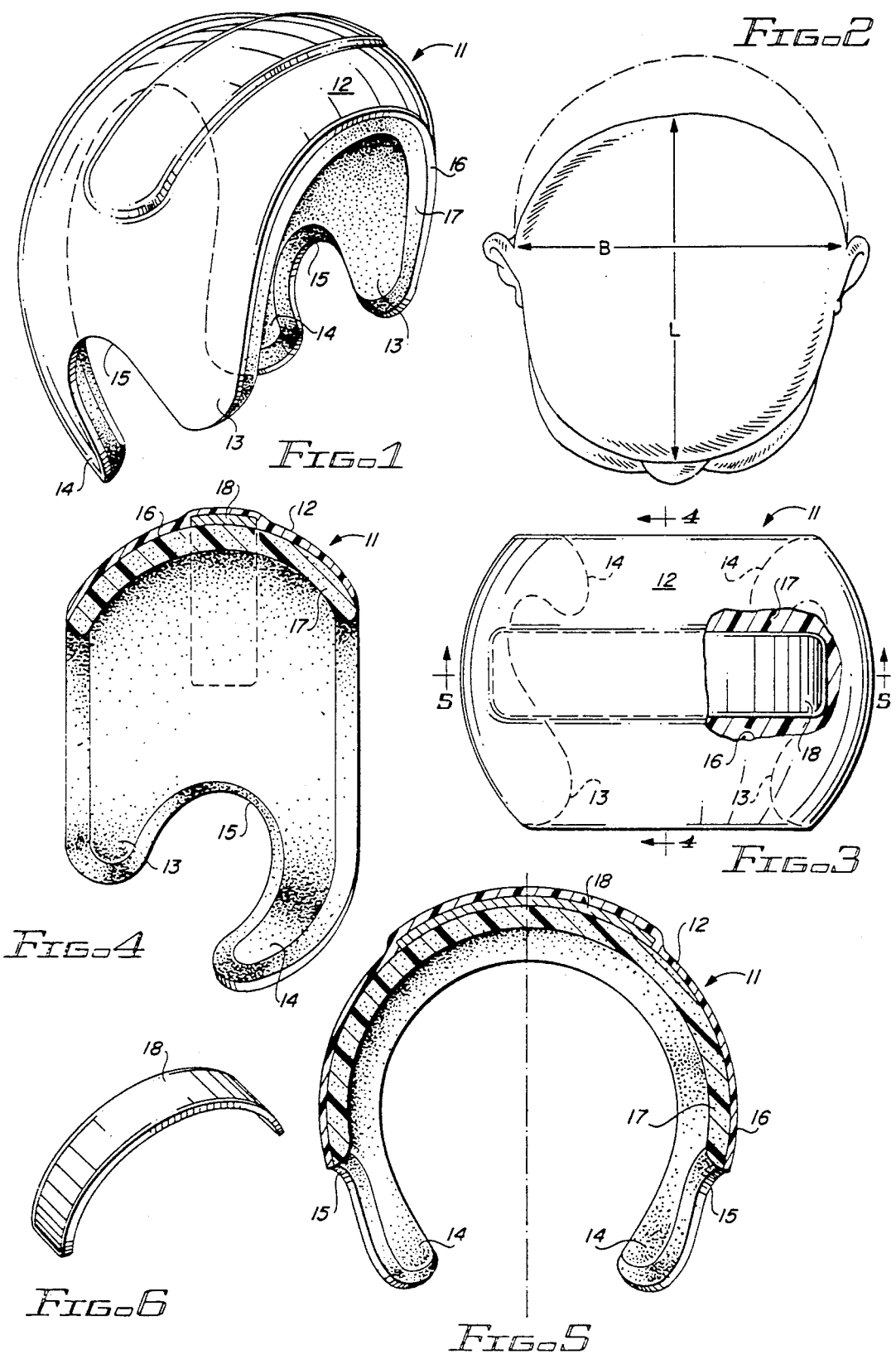

CRANIAL REMODELING ORTHOSIS

TECHNICAL FIELD

This invention is concerned with correcting brachycephalic cranial abnormalities in humans.

BACKGROUND ART

Otherwise normal children may be afflicted with cranial abnormalities, known as plagiocephaly, which also contribute to facial asymmetry. Such abnormalities are correctable, particularly if treatment is undertaken at an early age, preferably when the subject is less than six months old. The subject can thus be spared the indignity of going through life with a cosmetic disability.

In U.S. Pat. No. 5,094,229, granted Mar. 10, 1992, for "CRANIAL REMODELING ORTHOSIS", the present applicants discuss different approaches to cranial remodeling and disclose an improved cranial remodeling band for correcting plagiocephaly. Reference is made to the patent for further background art for the present invention.

The band orthosis of the '229 patent is effective for treatment of a variety of cranial abnormalities. However, it is believed that one particular form of abnormality can be corrected with somewhat different orthosis design and treatment methodology. This abnormality is known as brachycephalic cranial head shape abnormality. The brachycephalic head shape expresses itself as occipital flattening of the cranium with resultant biparietal breadth and/or height abnormalities usually accompanied by bi-temporal and frontal breadth abnormalities. The supernormal brachycephalic head shape is one in which the maximum cranial breadth departs from established anthropometric norms in being disproportionately large in relation to the maximum cranial length.

DISCLOSURE OF THE INVENTION

The orthosis of this invention acts to correct brachycephaly by constraining growth across the breadth and height of the cranium while encouraging an increase in the maximum cranial length. The orthosis is configured to extend across the top of a head with depending regions closely confining the temporal bone regions and the mastoid process regions of the cranium. The orthosis is self-suspending and preferably includes an elastic band for imparting ear-to-ear rigidity to the device.

BRIEF DESCRIPTION OF THE DRAWINGS

This invention is described in greater detail hereinafter by reference to the accompanying drawings, wherein:

FIG. 1 is a perspective view of an orthosis constructed in accordance with this invention;

FIG. 2 is a view of the top of an infant's head, illustrating the abnormality known as brachycephaly;

FIG. 3 is a top view of the orthosis with a portion broken away to show its construction;

FIG. 4 is a sectional view from the side of the orthosis, taken as indicated, by line 4—4 in FIG. 3;

FIG. 5 is a sectional view of the orthosis taken as indicated by line 5—5 in FIG. 3; and FIG. 6 is a perspective view of an elastic band employed in the orthosis.

BEST MODE FOR CARRYING OUT THE INVENTION

In the drawing, the numeral 11 is employed to indicate, generally, the orthosis of this invention. This orthosis is employed to correct the cranial abnormality known as "brachycephaly" which is illustrated in FIG. 2. Referring specifically to FIG. 2, the abnormality is manifested as a cranial condition in which the breadth "B" of the cranium is disproportionately large in relation to the length "L" of the cranium. The orthosis 11 is employed to remodel the cranium by allowing growth of the cranium length to the dot and dash configuration shown while constraining growth of the cranium in breadth.

The preferred configuration for the orthosis is illustrated in FIGS. 3-5. It comprises a central, or upper, region 12 which is shaped to extend over the top and closely conform to the configuration of the top of the cranium. For most subjects, this region 12 of the orthosis will cover an anterior region of the parietal bone and possibly a posterior region of the frontal bone. Depending upon the size of the cranium of the subject, this upper region 12 of the orthosis will have a front to back width of approximately four (4) to five (5) inches (10.16 to 12.7 cm.).

Integrally associated with the central region 12 of the orthosis are depending regions 13 and 14 on each side of the orthosis. Depending regions 13 are shaped to closely confine temporal bone regions of the cranium adjacent and forward of the ears of the subject. Depending regions 14 are shaped to closely confine mastoid process regions of the cranium to the rear and beneath the ears of the subject. Cut out regions 15 between depending regions 13 and 14 uncover the ears of the subject for his or her comfort.

It is important that the orthosis 11 be configured to be self-suspending, i.e., remain in stabilized position on the cranium of the subject without the aid of a chin strap. The latter aid, which is often required with helmet-type orthosis, is deemed undesirable because it can interfere with eating and possibly deform the subject's jaw bone.

Self-suspension of the orthosis 11 of this invention is achieved as a result of the close confinement of the temporal bone and mastoid process regions of the cranium by the depending regions 12 and 13 of the orthosis. The regions of contact formed by orthosis regions 12 and 13 fall within planes of the cranium which have circumferences which are less than the maximum occipitofrontal circumference of the subject's cranium. The inherent resiliency of the orthosis (which is discussed hereafter) draws the orthosis down with the central region 12 in contact with the top of the subject's head and holds the orthosis in place.

Orthosis 11 is constructed with an outer layer 16 of plastic material and an inner liner 17 of compressible foam material. For most infant and child orthoses, sheet plastic of co-polymer polypropylene material approximately 3/16" (4.76 mm) thick is suitable for forming the outer layer 16. This material is light in weight, possesses considerable strength, yet is resilient and is thermoformable to almost any desired shape. The preferred material for the liner 17 is sheet polyurethane foam having a thickness of approximately 3/8" (10 mm).

For treating many subjects, the inherent stiffness and resiliency of the outer layer 16 of polypropylene will be sufficient to hold the orthosis in place and effectively restrain growth across the breadth and height of the cranium. However, if desired, the ear-to-ear stiffness of the orthosis can be enhanced by incorporating stiffening means therein, preferably in the form of an arcuate elastic band 18 positioned in the upper region 12 of the orthosis. A carbon fiber material is preferred for the band 18 inasmuch as this material offers significant strength with very little weight. For the comfort of the subject, it is desirable to keep the weight of the orthosis as low as possible.

It can be appreciated that the orthosis 11 must be constructed to afford some flexibility to permit the opposite depending regions 13 and 14 to be spread apart to install and remove the orthosis from the subject's head.

For maximum effectiveness, the orthosis of this invention should be individualized for each subject. This means that each orthosis should be fabricated from an impression of the head of the subject of be treated.

The technique for fabricating an orthosis 11 involves forming a positive model of the subject's skull. This model can be constructed from a plaster of Paris negative mold of the head or from a digitized laser image of the head. The positive model is modified to the configuration desired for the remodeled cranium and then employed to shape the orthosis. The latter step involves draping the liner material 17 over the model and then vacuum thermoforming the outer layer material 16 over the model. The model is removed from this structure and the structure is trimmed to the configuration illustrated in the drawing and described above. If the elastic band 18 is to be employed, it is pre-shaped to the desired configuration and placed over the liner material 17 before the outer layer material 16 is thermoformed. This encases the band 18 between outer layer 16 and liner 17.

We claim:

1. A cranial remodeling orthosis comprising a resilient band adapted to extend across the parietal bone region of the cranium and having depending regions shaped to closely confine the temporal bone regions and the mastoid process regions of the cranium with relief areas therebetween to expose the ears of a patient wearing the orthosis, said depending regions of the orthosis being adapted to provide regions of contact which fall within planes of the cranium which have circumferences which are less than the maximum occipitofrontal circumference of the cranium whereby the orthosis is held in place on the cranium.

2. The orthosis of claim 1, further comprising, rigidity imparting means in the form of an elastic band within that portion of the orthosis band which is adapted to extend across the parietal region of the cranium.

3. The orthosis of claim 2, wherein said elastic band is formed from a carbon fiber material.

4. The orthosis of claim 2, further characterized in that said orthosis comprises an outer layer of thermoformed plastic material and an inner liner of cushioning material and said elastic band is disposed between said outer layer and said inner liner.

* * * * *